US00PP28356P3

(12) United States Plant Patent
Olesen

(10) Patent No.: US PP28,356 P3
(45) Date of Patent: Sep. 5, 2017

(54) FLORIBUNDA ROSE PLANT NAMED 'POULNAP004'

(50) Latin Name: ***Rosa* hybrid**
Varietal Denomination: Poulnap004

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 83 days.

(21) Appl. No.: 14/756,279

(22) Filed: Aug. 20, 2015

(65) Prior Publication Data

US 2017/0055402 P1 Feb. 23, 2017

(51) Int. Cl.
*A01H 5/02* (2006.01)

(52) U.S. Cl.
USPC ..... Plt./148

(58) Field of Classification Search
USPC ..... Plt./148
See application file for complete search history.

(56) References Cited

PUBLICATIONS

Floribunda rose plant named 'Poulnap004', http://www.poulsenroser.dk/media/73107/NATIONAL-PARKS-2013_LR_Poulsen-Roser.pdf, Apr. 2013.*

UPOV hit on floribunda rose plant named 'Poulnap004', QZ PBR 43434, Dec. 15, 2014.*

* cited by examiner

*Primary Examiner* — Anne Grunberg

(57) ABSTRACT

A new garden rose plant of the Floribunda class which has abundant, pink flowers and attractive foliage. This new and distinct variety has shown to be uniform and stable in the resulting generations from asexual propagation.

2 Drawing Sheets

Botanical designation: *Rosa* hybrid.
Variety denomination: 'Poulnap004'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2000 and the resulting seeds were planted in a controlled environment in Fredensborg, Denmark. The new variety, named 'Poulnap004', originated as a single seedling from the stated cross.

The new variety may be distinguished from its male pollen parent and female seed parent primarily by the following characteristics. The female seed parent is more compact in growth height than the new variety. The male pollen parent has flowers which are Red Group 36B while the new variety has flowers which are Red Group 49B.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulnap004' from all other varieties of which we are aware.

As part of the rose development program, Mogens N. Olesen germinated the seeds from the aforementioned hybridization during winter of 2000 and conducted evaluations on the resulting seedlings in a controlled environment in Fredensborg, Denmark. 'Poulnap004' was selected in the spring of 2001 by the inventor as a single plant from the progeny of the aforementioned hybridization.

Asexual reproduction of 'Poulnap004' by traditional budding and rooted cuttings was first done by Mogens N. Olesen in the nursery in Fredensborg, Denmark in July, 2001. This initial and other subsequent asexual propagations conducted in controlled environments have demonstrated that the characteristics of 'Poulnap004' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulnap004'.

Specifically illustrated in FIG. 1 are leaves, bare stems exhibiting thorns, petals detached, a cluster of flower buds on a branch, sepals detached, and reproductive flower parts.

Specifically illustrated in FIG. 2 is a cluster of open flowers. Plants shown are 1 year of age.

DETAILED DESCRIPTION OF THE VARIETY

The following is a description of 'Poulnap004', as observed in its growth in an open air container nursery in Denmark. Observed plants are 1 year of age, and were grown on their own roots in 23 cm containers. Color references are made using The Royal Horticultural Society (London, England) Colour Chart, 2001, except where common terms of color are used.

For a comparison, several physical characteristics of the rose variety 'Poulbella', U.S. Plant Pat. No. 12,904 are compared to 'Poulnap004' in Chart 1.

CHART 1

| | 'Poulnap004' | 'Poulbella' |
|---|---|---|
| Petal Count | 35 | 35-40 |
| Flower Diameter | 100 mm | 50-80 mm |
| General Tonality of Flower Color | Red Group 49B | Red-Purple Group 57C |

Flower and Flower Bud

Blooming habit: Continuous.

Flower bud:

*Size.*—Upon opening, 30 mm in length from base of receptacle to end of bud. Bud diameter is 14 mm.

*Bud form.*—Ovoid.

*Bud color.*—As sepals divide petals are Red Group 51B.

*Sepal inner surface.*—Color: Green Group 138C. Surface: Moderately pubescent.

*Sepal outer surface.*—Color: Green Group 143B with intonations of Greyed-Purple Group 183B. Texture: Rough.

*Sepal shape.*—Apex: Cirrhose. Base: Flat at union with receptacle.

*Sepal margin.*—Margins have weak foliaceous appendages on three of the five sepals.

*Sepal size.*—27 mm long, 10 mm wide.

*Receptacle.*—Texture: Smooth. Size: 7 mm in height, 7 mm wide. Color: Yellow-Green Group 144A. Shape: Campanulate.

*Pedicel.*—Surface: Smooth. Length: About 45 mm. Diameter: 3 mm on average. Color: Yellow-Green Group 144D. Strength: Moderate.

*Peduncle.*—Length: 5 to 25 cm. Diameter: About 3 to 4 mm. Color: Yellow-Green Group 146D. Texture: Smooth.

Flower bud development: Flower buds are borne in corymbs of 3 to 5 flower buds.

Flower bloom:

*Fragrance.*—Moderate old rose scent.

*Duration.*—The blooms have a duration on the plant of approximately 10 days. Petals fall cleanly away from plant after flowers have fully matured.

*Size.*—Flower diameter is 100 mm when open. Flower depth is 30 mm.

*Flower shape.*—Open cup, double flower, with petals that curve out from the center.

*Shape of flower, side view.*—The upper portion is flat. The lower portion is a flattened convex.

Petalage: Under normal conditions, flowers have 35 petals total, 10 of which are petaloids.

General tonality of flower: Open flowers are Red Group 49B.

*Petal color.*—Upon opening, inner and outer petals Upper surface: Red Group 49B. Lower surface: Red Group 49A. Basal petal spots, upon opening: Upper surface: Yellow Group 10A. Lower surface: Yellow Group 10B. After opening, inner and outer petals Upper surface: Red Group 49C. Lower surface: Red Group 49D. Basal petal spots, after opening: Upper surface: Yellow Group 11A. Lower surface: Yellow Group 11B.

Petals:

*Petal reflex.*—Weak.

*Margin.*—Entire with occasional cleft. No undulations.

*Shape.*—Generally ovate. Apex shape: Rounded. Base shape: Rounded.

*Size.*—45 mm (l)×45 mm (w).

*Texture.*—Smooth.

*Thickness.*—Average.

Petaloids:

*Size.*—20 mm (l) by 12 mm (w).

*Quantity.*—About 10.

*Shape.*—Irregular and asymmetric. The apex and base are acute.

*Color.*—Upper surface is Red Group 49B. Lower surface is Red Group 49A. Petaloid spots at the base are Yellow Group 10A at the upper surface. Yellow Group 10B at the lower surface.

Reproductive flower parts:

*Pollen.*—None observed.

*Anthers.*—Size: 3 mm in length. Color: Yellow-Orange Group 23A. Quantity: 130 on average.

*Filaments.*—Color: Yellow-Orange Group 20A. Length: 7 mm.

*Pistils.*—Length: 5 mm. Quantity: 75 on average.

*Stigmas.*—Color: Yellow Group 4C.

*Styles.*—Color: Yellow Group 4C. Location of stigmas: Level in location relative to the length of the filaments and the height of the anthers.

*Hips.*—None Observed.

Plant

Plant growth: Upright, bushy. Plants are 50 cm in height, and 40 cm wide.

Stems:

*Color.*—Juvenile growth: Yellow-Green Group 144D. Mature growth: Yellow-Green Group 146D.

*Length.*—On average, canes are 40 cm from the base of the plant to the flowering portion.

*Diameter.*—8 mm.

*Internodes.*—On mature canes about 40 mm between nodes.

*Surface texture.*—Young wood: Smooth. Older wood: Smooth.

Long prickles:

*Incidence.*—10 prickles per 10 cm of stem.

*Size.*—Average length of prickles on mature stems is x mm.

*Shape.*—Upper portion is concave. Lower portion is concave.

*Color.*—Juvenile prickles: Greyed-Red Group 179C. Mature prickles: Greyed-Red Group 180A.

Plant foliage:

*Compound leaf.*—160 mm (l)×110 (w).

*Quantity.*—2 or 3 leaves per 10 cm of stem on average.

*Leaf bearing angle to the stem.*—45 degrees.

*Color of mature foliage.*—Upper side: Yellow-Green Group 147A. Lower side: Green Group 138D.

Plant leaves and leaflets:

*Stipules*.—Size: 10 mm long, 7 mm wide. Quantity: 2 per compound leaf. Shape: Linear, slightly broad based with outward extending apices. Margins: Finely serrated. Color: Yellow-Green Group 146B.

*Petiole*.—Length: 25 mm. Diameter: 2 mm.

*Upper surface*.—Color: Yellow-Green Group 146B.

*Lower surface*.—Color: Yellow-Green Group 144A.

*Rachis*.—Length: About 25 mm. Upper surface: Color: Yellow-Green Group 146B.

*Lower surface*.—Color: Yellow-Green Group 144A. Observations: Smooth.

*Leaflet*.—Quantity: Normally 5 to 7 leaflets. Margins: Serrulate. Size: On average terminal leaflets are 60 mm long, 50 mm wide. Shape: Generally elliptical. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Floribunda rose class named 'Poulnap004', substantially as illustrated and described herein, due to its abundant pink flowers, disease resistance, and extended period of bloom.

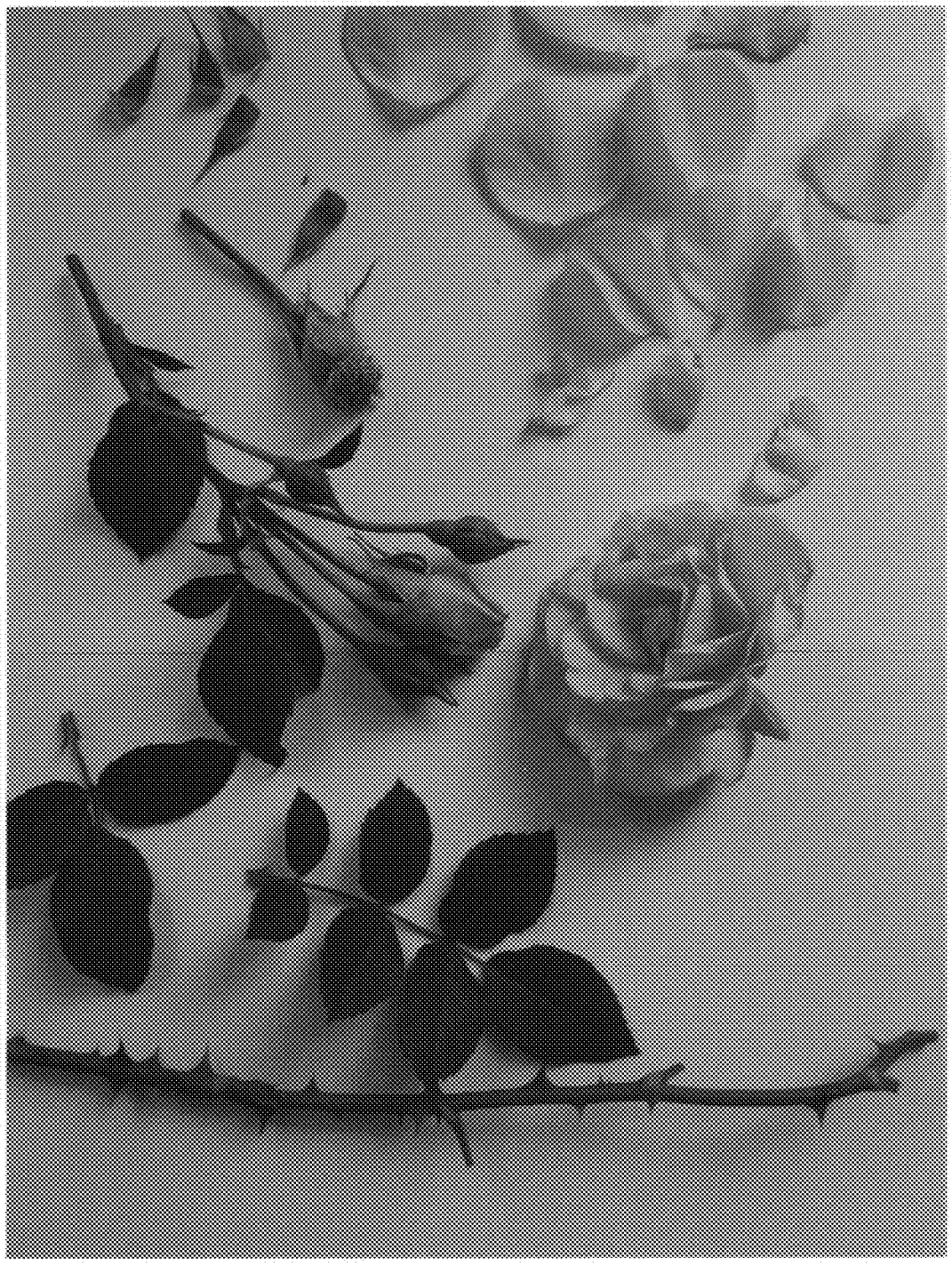

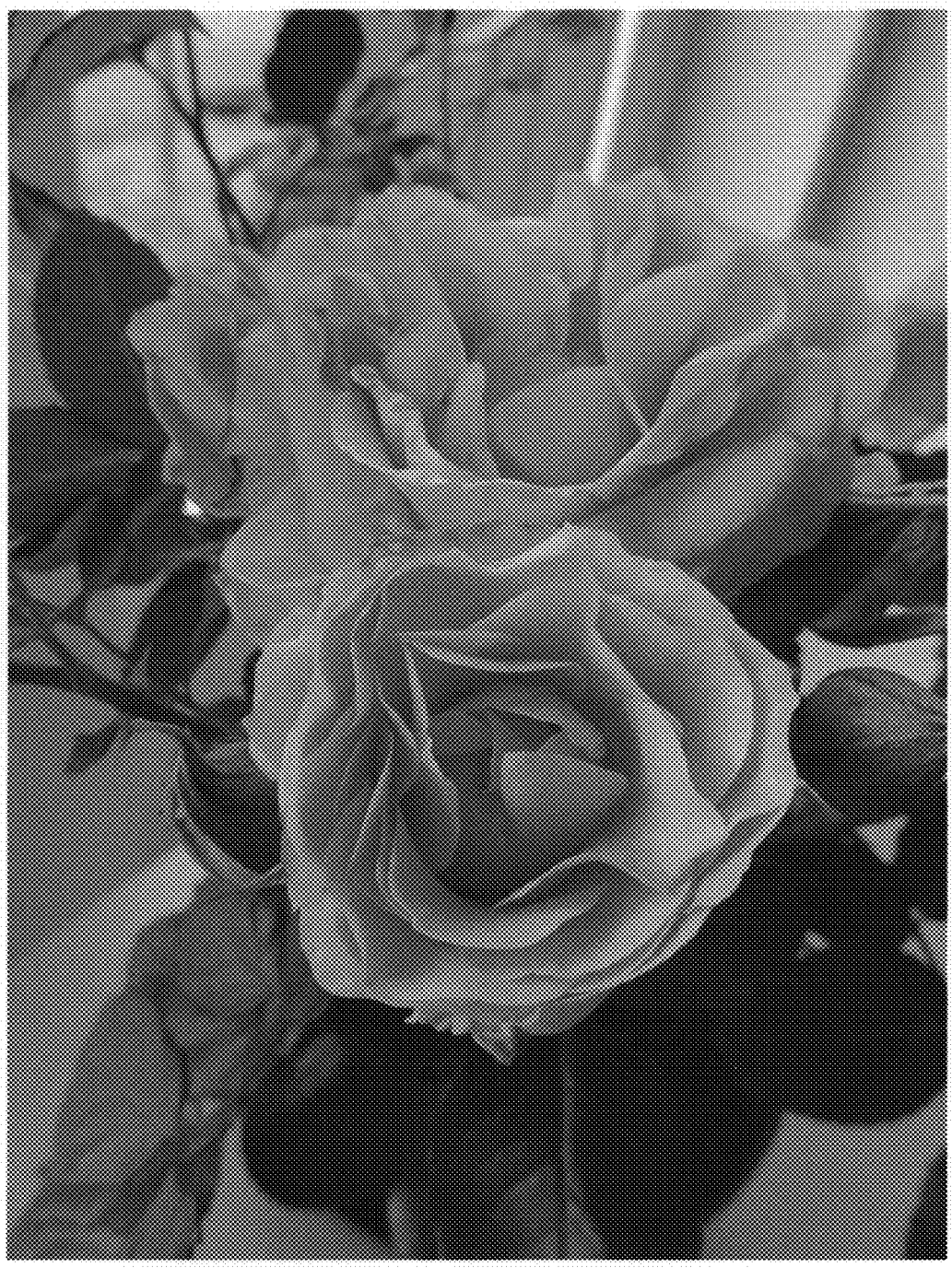

* * * * *